(12) United States Patent
Fagan et al.

(10) Patent No.: US 9,808,324 B2
(45) Date of Patent: Nov. 7, 2017

(54) CLEANING SYSTEM FOR REPROCESSING MEDICAL DEVICES

(71) Applicant: COVIDIEN LP, Mansfield, MA (US)

(72) Inventors: Lance Fagan, Bartow, FL (US); Steven Bragg, Winter Haven, FL (US); Seth Masek, Dover, FL (US); Jean-Paul Deeb, Land O Lakes, FL (US)

(73) Assignee: COVIDIEN LP, Mansfield, MA (US)

( * ) Notice: Subject to any disclaimer, the term of this patent is extended or adjusted under 35 U.S.C. 154(b) by 91 days.

(21) Appl. No.: 14/645,470

(22) Filed: Mar. 12, 2015

(65) Prior Publication Data

US 2015/0359599 A1 Dec. 17, 2015

Related U.S. Application Data

(60) Provisional application No. 62/011,132, filed on Jun. 12, 2014.

(51) Int. Cl.
*A61B 90/70* (2016.01)
*B08B 3/04* (2006.01)
(Continued)

(52) U.S. Cl.
CPC .............. *A61B 90/70* (2016.02); *A61B 1/121* (2013.01); *A61B 1/123* (2013.01); *A61B 17/29* (2013.01); *B08B 3/04* (2013.01); *A61B 18/1445* (2013.01)

(58) Field of Classification Search
None
See application file for complete search history.

(56) References Cited

U.S. PATENT DOCUMENTS 3,770,010 A 11/1973 Raefield
4,193,818 A 3/1980 Young et al.
(Continued)

FOREIGN PATENT DOCUMENTS

DE 10248460 A1 * 4/2004 ............... A61L 2/18
EP 2666427 A1 * 11/2013 ............. A61B 1/123
WO 2012/148266 A1 11/2012

OTHER PUBLICATIONS

European Search Report issued in corresponding application No. EP 15160513.6 on Nov. 4, 2015.
(Continued)

*Primary Examiner* — Michael Barr
*Assistant Examiner* — Cristi Tate-Sims

(57) ABSTRACT

A cleaning fixture for cleaning a medical device comprising a shaft receiving portion configured to receive a shaft and end effector assembly of the medical device, the shaft receiving portion including at least one nozzle disposed towards a distal end of the shaft receiving portion such that the at least one nozzle is positioned adjacent the end effector assembly of the medical device upon receipt of the shaft and end effector assembly of the medical device within the shaft receiving portion, and a handle receiving portion configured to receive the housing and handle of the medical device, the handle receiving portion releasably securable with the shaft receiving portion to enclose the medical device therein, the handle receiving portion including at least one lever activation assembly positioned adjacent the handle and operable to selectively actuate the handle to manipulate the end effector assembly.

7 Claims, 7 Drawing Sheets

(51) Int. Cl.
*A61B 1/12* (2006.01)
*A61B 17/29* (2006.01)
*A61B 18/14* (2006.01)

(56) References Cited

U.S. PATENT DOCUMENTS

| | | | |
|---|---|---|---|
| 4,299,244 A | 11/1981 | Hirai | |
| 4,741,351 A | 5/1988 | Minkin | |
| 5,279,799 A | 1/1994 | Moser | |
| 5,308,406 A | 5/1994 | Wallock et al. | |
| 5,310,524 A | 5/1994 | Campbell et al. | |
| 5,443,801 A | 8/1995 | Langford | |
| 5,489,531 A | 2/1996 | Benson | |
| 5,505,218 A | 4/1996 | Steinhauser et al. | |
| 5,554,228 A | 9/1996 | Giordano et al. | |
| 5,711,921 A | 1/1998 | Langford | |
| 5,716,454 A | 2/1998 | Carr | |
| 5,755,894 A | 5/1998 | Bowman et al. | |
| 5,761,069 A | 6/1998 | Weber et al. | |
| 5,921,256 A | 7/1999 | Barin | |
| 8,568,666 B2 | 10/2013 | Langford | |
| 2004/0118440 A1* | 6/2004 | Sasaki | A61B 90/70 134/166 C |
| 2014/0052135 A1 | 2/2014 | Aman et al. | |

OTHER PUBLICATIONS

"The EVOTECH(TM) Endoscope Cleaner and Reprocessor. The Next Generation in Flexible Endoscope Reprocessing", Advanced Sterilization Products, A Johnson & Johnson Company, Division of Ethicon; AD-53998 Rev. D, Ethicon, Inc. 2008.

Forte et al., "Comparative cost-efficiency of the EVOTECH endoscope cleaner and reprocessor versus manual cleaning plus automated endoscope reprocessing in a real-world Canadian hospital endoscopy setting", BMC Gastroenterology 2011, 11:105.

* cited by examiner

CLEANING SYSTEM FOR REPROCESSING MEDICAL DEVICES

CROSS REFERENCE TO RELATED APPLICATION

The present application claims the benefit of and priority to U.S. Provisional Application Ser. No. 62/011,132, filed on Jun. 12, 2014, the entire contents of which are incorporated herein by reference.

BACKGROUND

Technical Field

The present disclosure relates to reprocessing medical devices, and more particularly, to systems and methods for reprocessing medical devices.

Background of Related Art

Cleaning of medical devices is a known challenge in the field of medical device reprocessing. One challenge in particular is that medical devices usually require substantial disassembly prior to manual or mechanical cleaning. Such disassembly is undesirable because it is a time consuming process, increases the probability of damage, and decreases the fatigue life of the device parts. Another challenge in reprocessing is adequate cleaning. While reprocessing systems typically rely on delivering chemicals and kinetic energy, all surfaces and components of the devices are typically cleaned with the same energy in the same fashion. This is problematic because it can result in inadequate cleaning of the more heavily contaminated areas of the device.

SUMMARY

In accordance with aspects of the present disclosure, a cleaning fixture for reprocessing a medical device is provided. The cleaning fixture generally includes a shaft receiving portion configured to receive a shaft and end effector assembly of the medical device, the shaft receiving portion including at least one nozzle disposed towards a distal end of the shaft receiving portion such that the at least one nozzle is positioned adjacent the end effector assembly of the medical device upon receipt of the shaft and end effector assembly of the medical device within the shaft receiving portion; and a handle receiving portion configured to receive the housing and handle of the medical device, the handle receiving portion releasably securable with the shaft receiving portion to enclose the medical device therein, the handle receiving portion including at least one lever activation assembly positioned adjacent the handle and operable to selectively actuate the handle to manipulate the end effector assembly.

In aspects, the lever activation assembly includes a nozzle, an actuator, and a lever.

In aspects, the lever activation assembly is coupled to a valve system configured to supply a fluid, the lever activation assembly configured to actuate simultaneously and/or independently when the fluid is supplied to the lever activation assembly from the valve system.

In aspects, the at least one nozzle is disposed on the circumference of the shaft receiving portion.

In aspects, the shaft receiving portion is an elongate muzzle defining a longitudinal axis.

In aspects, the shaft receiving portion includes a keying member.

In aspects, the keying member is tailored to complement a portion of the medical device such that the medical device is securely seated within the handle receiving portion.

In accordance with other aspects of the present disclosure, an automated system for cleaning a medical device is provided. The system generally includes a cleaning fixture having a shaft receiving portion and a handle receiving portion, wherein at least one nozzle is disposed adjacent a distal end of the shaft receiving portion, and wherein a lever activation assembly is coupled to the handle receiving portion; a dosage device configured to provide a cleaning mixture; a valve system configured to selectively provide the cleaning mixture to the at least one nozzle of the cleaning fixture; and a controller configured to control at least one of the dosage device, the valve system, or actuation of the lever activation assembly.

In aspects, the controller is configured to control the dosage device, the valve system, and the lever activation system.

In aspects, the system further includes a fluid supply coupled to at least one of the dosage device or the valve system.

In aspects, the lever activation assembly is coupled to the valve system and is selectively actuatable in response to fluid being supplied thereto, and wherein the controller is configured to control the supply of fluid to the lever activation assembly.

In aspects, an air supply coupled to the valve assembly.

In aspects, the controller is configured to control the valve assembly to supply at least one of air, water, vacuum, or the cleaning mixture.

In accordance with other aspects of the present disclosure, a method of reprocessing a medical device is disclosed. The method generally includes, positioning a medical device within a cleaning fixture; supplying a cleaning mixture to the cleaning fixture; and activating a lever activation assembly of the cleaning fixture to manipulate an end effector assembly of the medical device to facilitate cleaning of the medical device with the cleaning mixture.

In aspects, supplying the cleaning mixture and activating the lever activation assembly are performed simultaneously and/or independently, e.g., intermittently or randomly.

In aspects, the method further includes controlling the supplying of the cleaning mixture and activating the lever activation assembly in accordance with a cleaning program.

In aspects, the method further includes mixing a fluid with at least one cleaning component to form the cleaning mixture prior to supplying the cleaning mixture.

In aspects, the method further includes draining the cleaning mixture from the cleaning fixture.

In aspects, the method further includes supplying air to the cleaning fixture to facilitate drying of the medical device.

In aspects, the method further includes supplying vacuum to the cleaning fixture to facilitate drying of the medical device.

BRIEF DESCRIPTION OF THE DRAWINGS

Various aspects of the present disclosure are described hereinbelow with reference to the drawings, wherein.

DETAILED DESCRIPTION

As described in more detail below, the present disclosure relates to systems and methods for reprocessing medical devices.

Figure 1:
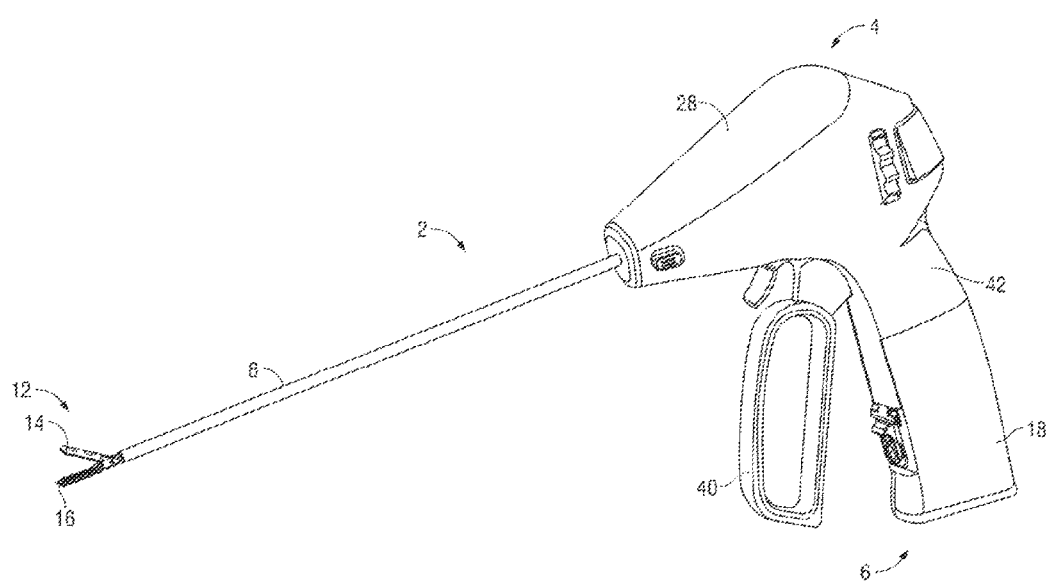
FIG. 1 is a side, perspective view of a battery-powered surgical instrument configured for use in accordance with the present disclosure.
Figure 2:
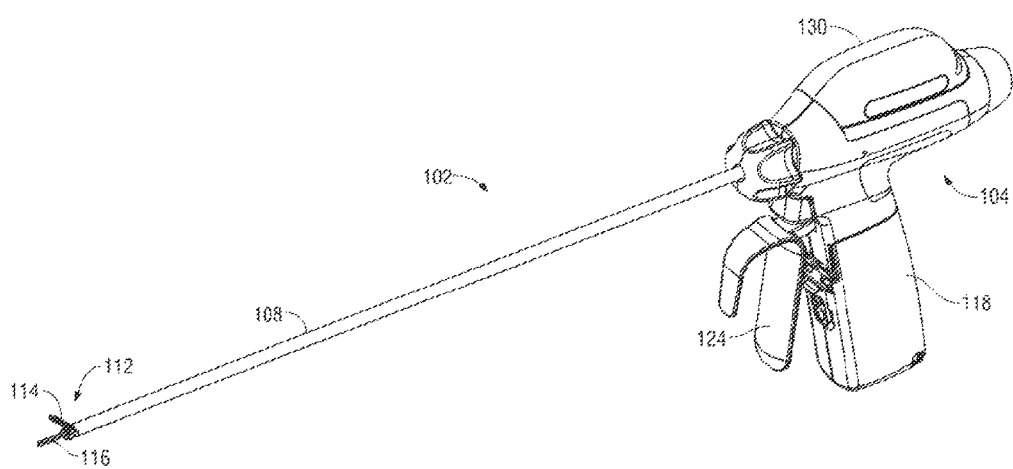
FIG. 2 is a side, perspective view of another battery-powered surgical instrument configured for use in accordance with the present disclosure.
Figure 3:
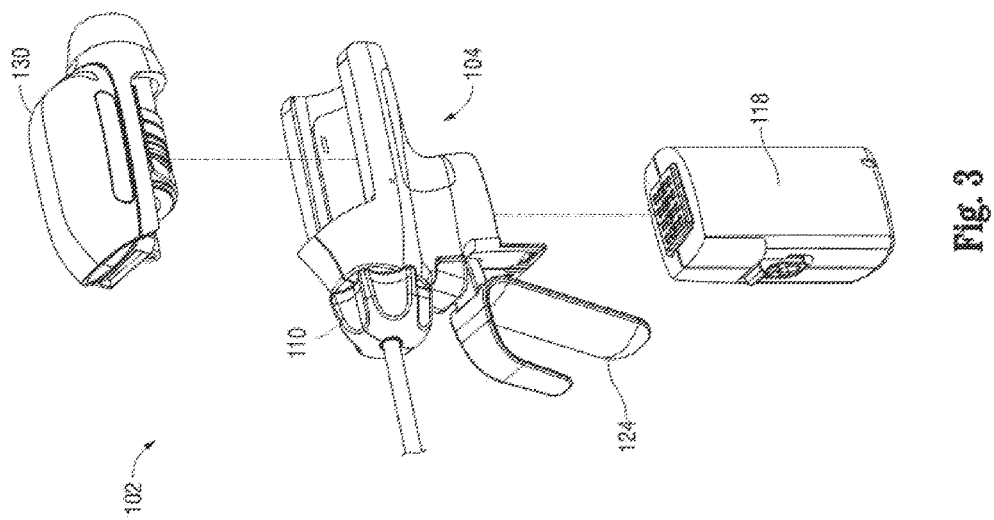
FIG. 3 is an exploded, perspective view of the proximal end of the surgical instrument of FIG. 2 shown with a battery assembly and a transducer and generator ("TAG") assembly separated from the housing.

Referring now to FIGS. 1-3, FIG. 1 depicts a portable, battery-powered electrosurgical instrument 2 and FIGS. 2-3 depict a portable, battery-powered ultrasonic surgical instrument 102. Although exemplary medical devices electrosurgical instrument 2 and ultrasonic surgical instrument 102 are detailed herein, the present disclosure is equally applicable for use in reprocessing any suitable medical devices. As such, electrosurgical instrument 2 and ultrasonic surgical instrument 102 are only summarily described herein.

With reference to FIG. 1, electrosurgical instrument 2, shown as an electrosurgical forceps, generally includes a housing 4, a battery assembly 18, an electrosurgical generator 28, a handle assembly 6, a shaft 8 defining a longitudinal axis, and an end effector assembly 12.

Handle assembly 6 includes a moveable handle 40 that is movable relative to a fixed handle portion 42 for moving jaw members 14, 16 of end effector assembly 12 between an open position and a clamping position for grasping tissue therebetween. Generator 28 is powered by battery assembly 18 and is configured to supply electrosurgical energy to one or both of jaw members 14, 16 for electrosurgically treating tissue grasped therebetween.

Referring now to FIGS. 2-3, ultrasonic instrument 102 includes components similar to that of electrosurgical instrument 2 (FIG. 1), namely, a housing 104, a battery assembly 118, a transducer and generator ("TAG") assembly 130, a shaft 108, and an end effector assembly 112.

Housing 104 is configured to releasably engage battery assembly 118 and TAG assembly 130 thereon. Shaft 108 extends distally from housing 104 defining a longitudinal axis. Shaft 108 further includes an end effector assembly 112 disposed at a distal end thereof. End effector assembly 112 includes a movable jaw 114 and a waveguide 116. A moveable handle 124 is operatively connected to housing 104 and is configured to move jaw 114 relative to waveguide 116 between an open position and a clamping position for grasping tissue therebetween. A distal collar 110 is coupled to housing 104 and end effector assembly 112 for selectively rotating end effector assembly 112 relative to housing 104. TAG assembly 130 is powered by battery assembly 118 and is configured to supply ultrasonic energy to waveguide 116 of end effector assembly 112 for ultrasonically treating tissue grasped between waveguide 116 and movable jaw 114.

With general reference to FIGS. 1-3, as can be appreciated, in the surgical arena as well as in other fields, it is important to protect the electronic components, e.g., the internal components of battery assemblies 18, 118, generator 28, and TAG assembly 130 from fluids, chemicals, temperatures, and/or adverse conditions such as those that may be present in the sterilization environment. Therefore, battery assemblies 18, 118, generator 28, and TAG assembly 130 are removed from their respective instruments 2, 102 prior to cleaning.

Figure 4:
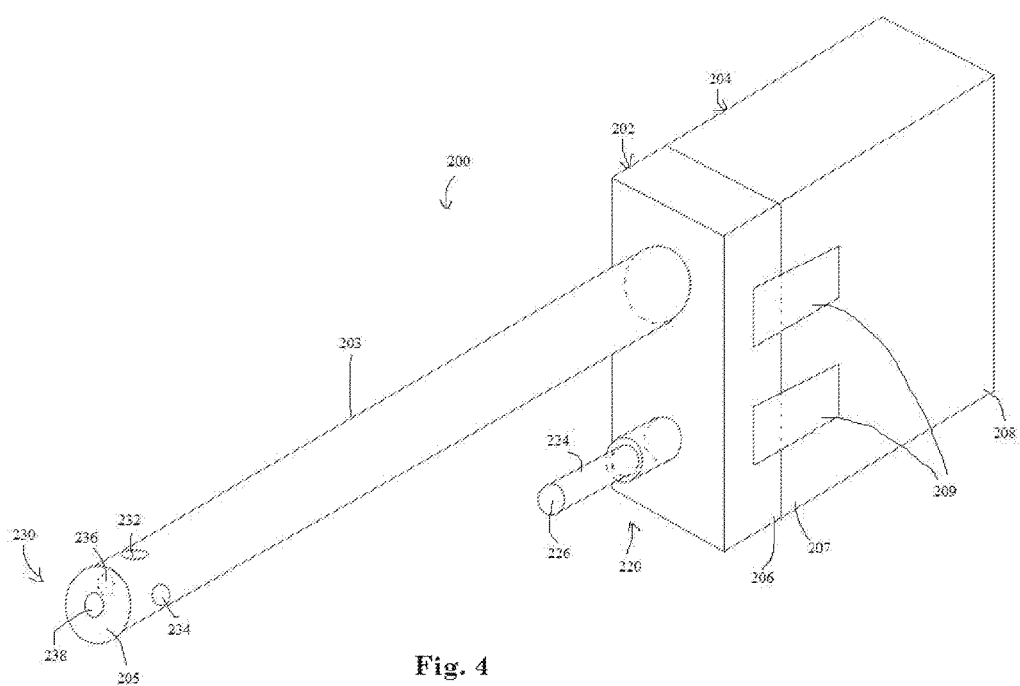
FIG. 4 is a perspective view of an illustrative embodiment of a cleaning fixture provided in accordance with the present disclosure.
Figure 5:
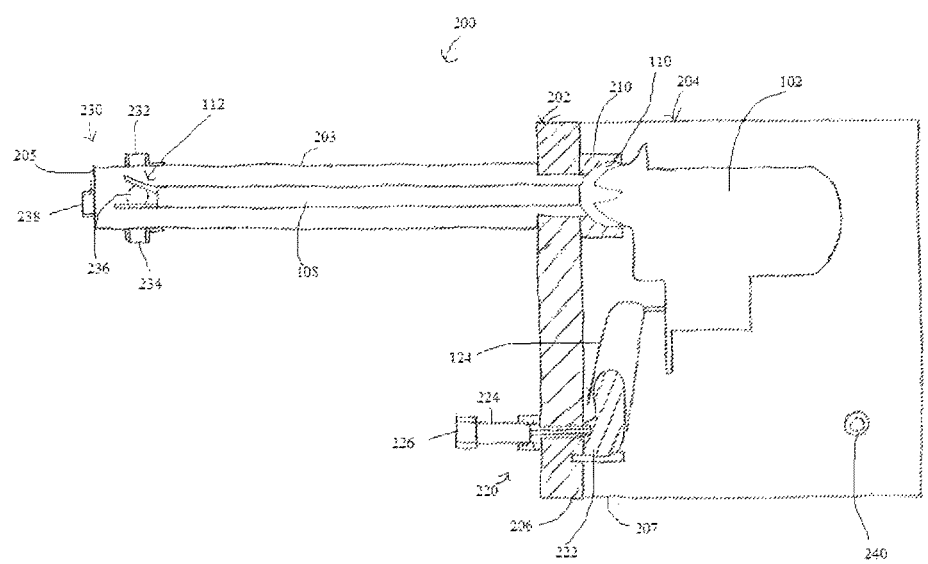
FIG. 5 is a longitudinal, cross-sectional view of the cleaning fixture of FIG. 4 including the surgical instrument of FIG. 2 disposed therein.

Referring now to FIGS. 4 and 5, a cleaning fixture provided in accordance with the present disclosure is shown generally as cleaning fixture 200. Cleaning fixture 200 is shown housing ultrasonic surgical instrument 102 therein (see FIG. 5) for cleaning of ultrasonic surgical instrument 102. However, as can be appreciated, cleaning fixture 200 may similarly be configured for use with electrosurgical instrument 2 (FIG. 1), or any other suitable medical device. Obviously, different configurations and considerations apply in providing a cleaning fixture 200 for a particular type of device; however, the aspects and features of the present disclosure remain generally consistent regardless of the particular device for which the cleaning fixture 200 is configured. It is also contemplated that a generic cleaning fixture be provided to enable cleaning of any one of a variety of different medical devices. Such a generic cleaning fixture may include interchangeable and/or adaptable components configured to achieve various different configurations to accommodate various different medical devices.

With reference to FIG. 4, cleaning fixture 200 includes a shaft receiving portion 202 and a handle receiving portion 204. Both shaft and handle receiving portions 202, 204, respectively, have a distal and a proximal end. Shaft receiving portion 202 includes a proximal section 206 at the proximal end thereof that is releasably secured to the distal end 207 of handle receiving portion 204 by fastening members 209. Fastening members 209 may include latches or any other suitable releasable fastening mechanism. Proximal section 206 of shaft receiving portion 202 and handle receiving portion 204, when fastened to one another, cooperate to define an enclosure for retaining housing 104 of surgical instrument 102 therein (see FIG. 5), as detailed below.

With additional reference to FIG. 5, shaft receiving portion 202 includes an elongate muzzle 203 extending distally from proximal section 206. Elongate muzzle 203 defines a longitudinal axis and includes a lumen extending longitudinally therethrough. The lumen of muzzle 203 has a diameter dimensioned such that end effector assembly 112 and shaft 108 may be inserted through the lumen of muzzle 203 in spaced relation relative to the inner surface of muzzle 203. The length of muzzle 203 is formed to be approximately the combined length of shaft 108 and end effector assembly 112 of surgical instrument 102 to fully accommodate such therein.

Proximal section 206 of shaft receiving portion 202, as mentioned above, is configured to be releasably secured to handle receiving portion 204, e.g., via fastening member 209. Further, proximal section 206 includes a keying member 210 that is tailored to receive distal collar 110 (or other suitable component) of surgical instrument 102 to retain surgical instrument 102 in a substantially fixed position within cleaning fixture 200. Keying member 210 is tailored to be a complementary structure to collar 110 such that keying member 210 is securely mated with collar 110. In the illustrated embodiment, collar 110 generally defines star-like configuration having a plurality of radially-spaced protrusions extending therefrom and keying member 210 defines a plurality of radially-spaced recesses each configured to receive one of the protrusions. As a result of this configuration, when collar 110 of surgical instrument 102 is seated into keying member 210, surgical instrument 102 is maintained in position where the longitudinal axis of shaft 108 is disposed in substantially coaxial alignment with the longitudinal axis of muzzle 203. However, keying member 210 may be custom tailored (or a plurality of interchangeable keying members 210 may be provided) to complement other types of distal collars to accommodate other medical devices within cleaning fixture 200.

Shaft receiving portion 202 of cleaning fixture 200 further includes a nozzle system 230 disposed towards the distal end 205 of shaft receiving portion 202. Nozzle system 230 may be operatively connected to a valve system 500 (FIG. 6) by one or more lines (not explicitly shown), although any other suitable connector(s) for delivering fluid to nozzle system 230 may be provided.

Nozzle system 230 is coupled to the outer surface of muzzle 203 and defines at least one inlet that provides access to the interior lumen of muzzle 203. Specifically, nozzles 232, 234, 236 are disposed annularly about the circumference of muzzle 203 to direct the flow of fluid from nozzles 232, 234, 236 radially inwardly into the lumen of muzzle 203 towards the longitudinal axis of surgical instrument 102, and radially about end effector assembly 112 and/or to withdraw fluids therefrom. Another nozzle 238 is disposed on the closed distal end 205 of shaft receiving portion 202 and likewise defines an inlet that provides access to the interior lumen of muzzle 203. Nozzle 238 is configured to direct the flow of fluid from nozzle 238 coaxially along the longitudinal axis of surgical instrument 102 in a proximal direction towards end effector assembly 112 and/or therefrom. Although nozzle system 230 is described as having four nozzles 232, 234, 236, 238, this is for exemplary purposes only as it is contemplated that nozzle system 230 may include any suitable number of nozzles provided in any suitable configuration.

Still referring to FIGS. 4 and 5, shaft receiving portion 202 further includes a lever activation assembly 220 disposed on proximal section 206 thereof. Lever activation assembly 220 has a lever 222, an actuator, e.g., a cylinder 224, and a nozzle 226. Lever 222 is positioned such that, when surgical instrument 102 is disposed within cleaning fixture 200, movable handle 124 of surgical instrument 102 is straddled over lever 222. The actuator may be a cylinder 224 such as a hydraulic cylinder, pneumatic cylinder, other suitable cylinder, or other suitable actuator.

Nozzle 226 is configured to be operatively connected to valve system 500 (FIG. 6) by any suitable connector (not explicitly shown) to deliver fluid pressure to cylinder 224. When fluid is delivered from valve system 500, through nozzle 226, to cylinder 224, cylinder 224 is actuated and urges lever 222 from a first position to a second position. Such movement of lever 222, in turn, actuates moveable handle 124 to thereby manipulate end effector assembly 112 from the open position to the clamping position. On the other hand, ceasing the delivery of fluid or a reduction of fluid delivery to nozzle 226 results in lever 222 returning from the second position back to the first position and, thus, urging moveable handle 124 to manipulate end effector assembly 112 from the clamped position back to the open position. The amount and frequency of manipulation of end effector assembly 112 is controlled via the fluid pressure cycle delivering fluid from valve system 500 to lever activation assembly 200 and may be selected based upon the particular configuration of the instrument, the type of cleaning being effected, experimental data, and/or other factors. As an alternative to a cylinder-based activation assembly 200, other suitable mechanisms, e.g., motors, may also be provided for mechanically urging movement of movable handle 124.

Handle receiving portion 204 of cleaning fixture 200, as noted above, is configured to receive housing 104 of the surgical instrument 102 and further includes one or more flushing ports 240. Each flushing port 240 is operatively connected to any suitable connector, e.g., a hose, to carry fluid from cleaning fixture 200 to a drain or other outlet (not explicitly shown).

Figure 6:
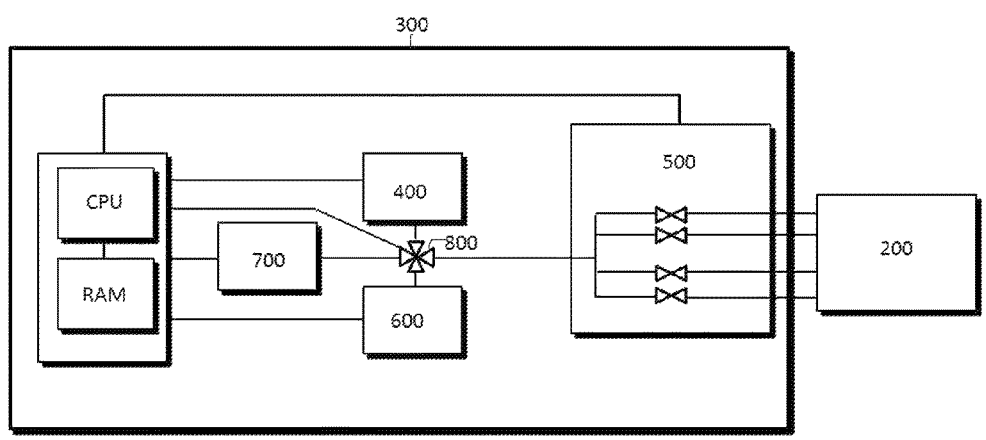
FIG. 6 is a schematic diagram of a system for cleaning medical devices provided in accordance with the present disclosure.

Turning to FIG. 6, cleaning fixture 200 is operatively connected to a control box 300. In some embodiments, control box 300 is configured to connect to a plurality of cleaning fixtures 200 to facilitate simultaneous cleaning of multiple medical devices (similar or different). However, for purposes of simplicity, control box 300 is described herein as configured for use with a single cleaning fixture 200.

Control box 300 includes a dosage control system 400, valve system 500, an air supply 600, a vacuum source 700, and a multidirectional valve 800. Dosage control system 400 is coupled to a fluid supply, e.g., a water supply (not shown), for mixing with one or more chemicals, cleaning compounds, etc. stored within or input into dosage control system 400. Such chemicals and cleaning compounds may include, for example, enzymatic compounds, detergents, disinfectants, etc. Dosage control system 400 may additionally be configured to simply provide the fluid from the fluid supply without adding any chemicals, e.g., during a flushing or rinsing stage, and may further include one or more heaters (not specifically shown) for heating the fluid and/or mixture to be supplied to a desired temperature to facilitate cleaning.

Control box 300 further includes a CPU and memory, e.g., a RAM, that executes and stores one or more cleaning programs, respectively. The CPU is operatively connected to dosage system 400, valve system 500, air supply 600, vacuum source 700 and multidirectional valve 800. Multidirectional valve 800 may be configured as a four way ball valve, although any other suitable valve may be provided including multidirectional valves different in number. Multidirectional valve 800 is operatively connected to valve system 500, air supply 600, and vacuum source 700. It is envisioned that during execution of the cleaning program, multidirectional valve 800 will switch between two of more of: supplying valve system 500 with the mixture from dosage system 400, supplying air from air supply 600, and removing moisture, fluids, and/or residue with vacuum source 700. During use, the CPU may direct dosage system 400 to provide an appropriate mixture of fluid and/or chemicals, cleaning compounds, etc., depending upon the cleaning program. Alternatively, dosage system 400 may include separate control electronics for these purposes.

Valve system 500 includes four valves; however, as aforementioned, the number of valves may vary. Each valve included in valve system 500 is operatively connected to cleaning fixture 200 and supplies cleaning fixture 200 with the chemical/fluid mixture or a fluid (e.g., water or air), depending on the particular stage of the cleaning program.

Figure 7:
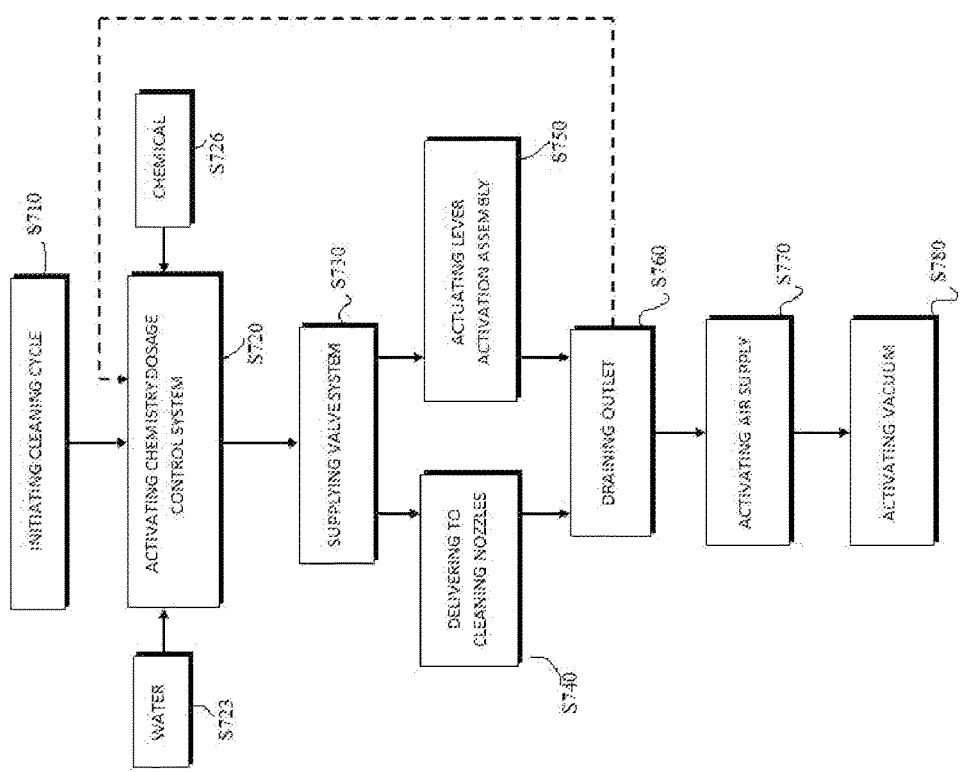
FIG. 7 is a flow diagram illustrating a method of cleaning medical devices provided in accordance with the present disclosure.

Turning now to FIG. 7, in conjunction with FIGS. 4-6, the use and operation of cleaning fixture 200 for cleaning surgical instrument 102 is detailed. Although detailed with respect to cleaning fixture 200 and surgical instrument 102 for exemplary purposes, the methods detailed herein are equally applicable for use with other cleaning fixtures and/or for cleaning other medical devices. As noted above, control box 300 controls the various different stages of cleaning, although any or all of the cleaning stages may alternatively be controlled via any other suitable control and/or may be manually controlled.

Initially, as indicated in S710, the desired cleaning cycle is selected and initiated, e.g., by an operator pushing a button, touch screen, or other activator. As can be appreciated, in embodiments where cleaning fixture 200 is configured to clean various different medical devices and/or medical devices used in different procedures, different cleaning programs may be provided depending on the particular situation. The CPU of control box 300 receives the initiation signal corresponding to the selected cleaning program and, in response, initiates that cleaning program.

Once activated, as indicated in S720, dosage control system 400, under direction of the CPU, draws water (or other fluid), as indicated in S723, and the appropriate chemical(s), compounds, etc. as indicated in S726, into dosage control system 400 and creates a mixture. The mixture is then supplied from dosage control system 400 to valve system 500, as indicated in S730.

Next, valve system 500 delivers the mixture to cleaning nozzles 230, as indicated in S740, and/or lever activation assembly 220 to actuate lever activation assembly 220, as indicated in S750. Alternatively, fluid and/or the mixture may separately and independently be delivered to lever activation assembly 220, or lever activation assembly 220 may be independently actuated (e.g., in embodiments where lever activation assembly 220 is actuated by a motor or other suitable mechanism). Valve system 500, under direction of the CPU, controls the amount of mixture delivered, the pressure at which the mixture is delivered, and the temperature the mixture is delivered to both nozzles 230 and lever activation assembly 220. CPU may also control the separate and/or independent actuation of lever activation assembly 220 where a motor or other suitable mechanism is utilized to actuate lever activation assembly 220.

Draining of the mixture and/or fluid within cleaning fixture 200 may be effected, as indicated in S760, via opening the one or more flushing ports 240 and/or supplying water to cleaning fixture 200 (without added chemicals).

Depending upon the particular cleaning program employed, one or more of S720 through S760 may be repeated any number of times in any order to, for example, provide multiple stages of cleaning (with the same or different chemical mixtures), enable flushing between stages of cleaning, or for other purposes.

Following the cleaning and rinsing stages detailed above, multidirectional valve 800 is manipulated and the air supply 600 activated, as indicated in S770, to supply air to cleaning fixture 200 (through the various nozzles thereof) to dry surgical instrument 102. The air supplied to the cleaning fixture 200 may be heated or ambient temperature, depending on a particular purpose or cleaning protocol.

Following the cleaning, rinsing, and air supply stages (or intermediate thereof, e.g., as a final component of the drying stage), multidirectional valve 800 is manipulated and vacuum source 700 is activated, as indicated in S780, such that a vacuum is created to remove any cleaning residue, residual moisture, and/or other fluids from the cleaning fixture 200. At the completion of cleaning and drying, surgical instrument 102 is removed from the cleaning fixture 200 and may be reassembled for further use or repackaged.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limited, but merely as exemplifications of particular embodiments. Those skilled in the art will envision other modifications within the scope and spirit of the claims appended hereto.

What is claimed is:

1. A cleaning fixture for cleaning a medical device having a housing, a shaft extending distally from the housing, an end effector assembly disposed at the distal end of the shaft, and a handle coupled to the housing and operable to effect manipulation of the end effector assembly, the cleaning fixture comprising:
   a shaft receiving portion configured to receive the shaft and end effector assembly of the medical device, the shaft receiving portion including:
      an elongate muzzle defining a longitudinal axis; and
      at least one nozzle disposed towards a distal end of the elongate muzzle such that the at least one nozzle is positioned adjacent the end effector assembly of the medical device upon receipt of the shaft and end effector assembly of the medical device within the shaft receiving portion; and
   a handle receiving portion configured to receive the housing and handle of the medical device, the handle receiving portion releasably securable with the shaft receiving portion to enclose the medical device therein, the handle receiving portion including at least one lever activation assembly positioned adjacent the handle and operable to selectively actuate the handle to manipulate the end effector assembly.

2. The cleaning fixture of claim 1, wherein the lever activation assembly includes:
   a lever configured to be operably coupled to the handle of the medical device;
   an actuator movably coupled to the shaft receiving portion and operably coupled to the lever such that movement of the actuator relative to the shaft receiving portion actuates the handle of the medical device; and
   a nozzle attached to the actuator and configured to receive fluid therein for actuating the actuator.

3. The cleaning fixture of claim 2, wherein the nozzle is coupled to a valve system configured to supply the fluid to the nozzle to actuate the actuator.

4. The cleaning fixture of claim 1, wherein the shaft receiving portion includes a keying member disposed within a cavity cooperatively defined by the shaft receiving portion and the handle receiving portion, the keying member configured to detachably connect to the medical device.

5. The cleaning fixture of claim 4, wherein the keying member has a mating surface configured to mate with a corresponding mating surface on a portion of the medical device such that the medical device is securely seated within the cavity.

6. The cleaning fixture of claim 1, wherein the elongate muzzle of the shaft receiving portion extends distally from the handle receiving portion.

7. The cleaning fixture of claim 1, wherein the elongate muzzle has a distal end portion configured to enclose the end effector assembly of the medical device.

\* \* \* \* \*